United States Patent
Wu

(10) Patent No.: US 10,888,536 B1
(45) Date of Patent: Jan. 12, 2021

(54) METHOD OF IMPROVEMENT OF INSULIN SENSITIVITY IN OBESE PATIENTS

(71) Applicant: FOOYIN UNIVERSITY, Kaohsiung (TW)

(72) Inventor: Ming-Hsiu Wu, Kaohsiung (TW)

(73) Assignee: FOOYIN UNIVERSITY, Kaohsiung (TW)

(*) Notice: Subject to any disclaimer, the term of this patent is extended or adjusted under 35 U.S.C. 154(b) by 0 days.

(21) Appl. No.: 16/553,822

(22) Filed: Aug. 28, 2019

(51) Int. Cl.
*A61K 31/16* (2006.01)
*A61K 31/164* (2006.01)
*A61P 3/10* (2006.01)
*A61K 9/00* (2006.01)

(52) U.S. Cl.
CPC .......... *A61K 31/164* (2013.01); *A61K 9/0053* (2013.01); *A61P 3/10* (2018.01)

(58) Field of Classification Search
CPC ................................ A61K 31/16; A61K 31/00
See application file for complete search history.

(56) References Cited

FOREIGN PATENT DOCUMENTS

CN 105267191 A 1/2016

OTHER PUBLICATIONS

U.S. Food and Drug Administration, HHS. Center for Drug Evaluation and Research (CDER), "Guidance for Industry, Estimating the Maximum Safe Starting Dose in Initial Clinical Trials for Therapeutics in Adult Healthy Volunteers", Jul. 2005.

*Primary Examiner* — Samira J Jean-Louis
(74) *Attorney, Agent, or Firm* — WPAT, PC

(57) ABSTRACT

A method for improving insulin sensitivity in obesity-induced metabolic syndrome by administering propanamide to a subject in need thereof the increase of ATP synthesis, decreasing inflammation, reducing accumulation of visceral fat and improving hyperglycemia and hyperinsulinemia. Propanamide can be orally administered to the subject. Propanamide can be administered to the subject in a dosage of 11.56-15.38 mg/kg/day. Propanamide can be administered to the subject postprandially.

4 Claims, 5 Drawing Sheets

METHOD OF IMPROVEMENT OF INSULIN SENSITIVITY IN OBESE PATIENTS

BACKGROUND OF THE INVENTION

1. Field of the Invention

The present invention generally relates to a method of improvement of insulin sensitivity in obese patients and, more particularly, to a method for increasing activity of ATP synthesis, anti-inflammation, reducing accumulation of visceral fat, and preventing obesity-induced hyperglycemia and hyperinsulinemia by using propanamide.

2. Description of the Related Art

Mitochondrion, an organelle found in eukaryotic organisms, is responsible for most of the useful energy derived from the breakdown of carbohydrates and fatty acids, which is converted to adenosine triphosphate (ATP). The insufficient activity of mitochondrion may result in obesity, metabolic syndrome, insulin resistance and even type II diabetes. Moreover, in obese person, a high level of serum endotoxins (such as lipopolysaccharides) from gut and fat tissue secrets inflammatory cytokines (such as tumor necrosis factor-a; TNF-α) cause chronic inflammation, which also cause insulin resistance and increases blood glucose level. Insulin resistance is defined as a pathological condition in which cells fail to respond normally to insulin, and is especially associated with metabolic syndrome. Thus, inhibition of the inflammation in the obese person decreases insulin resistance and lower blood glucose level. However, there is currently no method for increase of ATP synthesis, reducing inflammation, preventing accumulation of visceral fat, improving glucose tolerance and insulin sensitivity.

SUMMARY OF THE INVENTION

It is therefore an objective of the present invention to provide a method for increase of ATP production, anti-inflammation, reducing accumulation of visceral fat, improving glucose tolerance and insulin sensitivity by using propanamide.

One embodiment of the present invention discloses a method of improvement of insulin sensitivity in obese patients including administering propanamide to a subject in need thereof for increase of ATP synthesis activity, decreasing inflammation, reducing accumulation of visceral fat and improving obesity-induced hyperglycemia and hyperinsulinemia. As an example, propanamide can be administered to the subject in a dosage of 11.56-15.38 μg/kg/day, and can be orally administered to the subject postprandially.

Accordingly, the use of propanamide can effectively increase ATP synthesis, decrease inflammation, reduce accumulation of visceral fat and ameliorate obesity-induced hyperglycemia and hyperinsulinemia.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

DETAILED DESCRIPTION OF THE INVENTION

Figure 1:
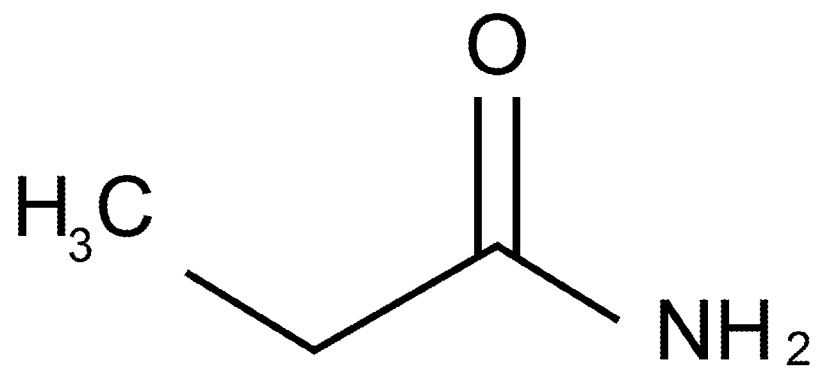
FIG. 1 depicts a chemical formula of propanamide.

The term "propanamide" according to the present invention refer to a chemical material with a chemical formula shown in FIG. 1. Propanamide is usually used to provide an amide group (—$CONH_2$) for synthesis of certain chemicals. No medical report related to propanamide is present.

Propanamide can increase ATP level, decrease inflammation in macrophage, reduce accumulation of visceral fat, and improve obesity-induced hyperglycemia and insulin resistance in mice and rats. Therefore, propanamide can be applied to attenuate insulin resistance in obesity-induced metabolic syndrome. Propanamide can be used individually, or in combination with pharmaceutical acceptable vehicles, excipients, or other nutrients, being in a composite. In addition, propanamide can be further manufactured into any oral type that is easy to take, such as pastil, capsule, powder, pill, solution, or fermented products. Yet, propanamide can be combined with other food products or drinks, being manufactured into a more convenient type for taking.

In addition, propanamide can be administered to a subject in need thereof. As an example, propanamide can be administered in an effective amount of 11.56-15.38 μg/kg/day, such as orally administered to the subject postprandially. As such, propanamide can play the role in the subject.

Trial (A).

To evaluate propanamide can increase of ATP synthesis, mouse macrophage (J774A.1 cell line) was used as the cell model. The J774A.1 cells of groups A1-A5 were treated by propanamide shown in TABLE 1 for 6 hours. The J774A.1 cells without treatment were used as group A0. ATP level in the J774A.1 cells of groups A0-A5 were analyzed by ATP luminometer, respectively. The unit of ATP level is relative light unit (R.L.U).

TABLE 1

| Group | propanamide (μM) |
|---|---|
| A0 | 0 |
| A1 | 0.04 |
| A2 | 0.4 |
| A3 | 4 |
| A4 | 40 |
| A5 | 400 |

Figure 2:
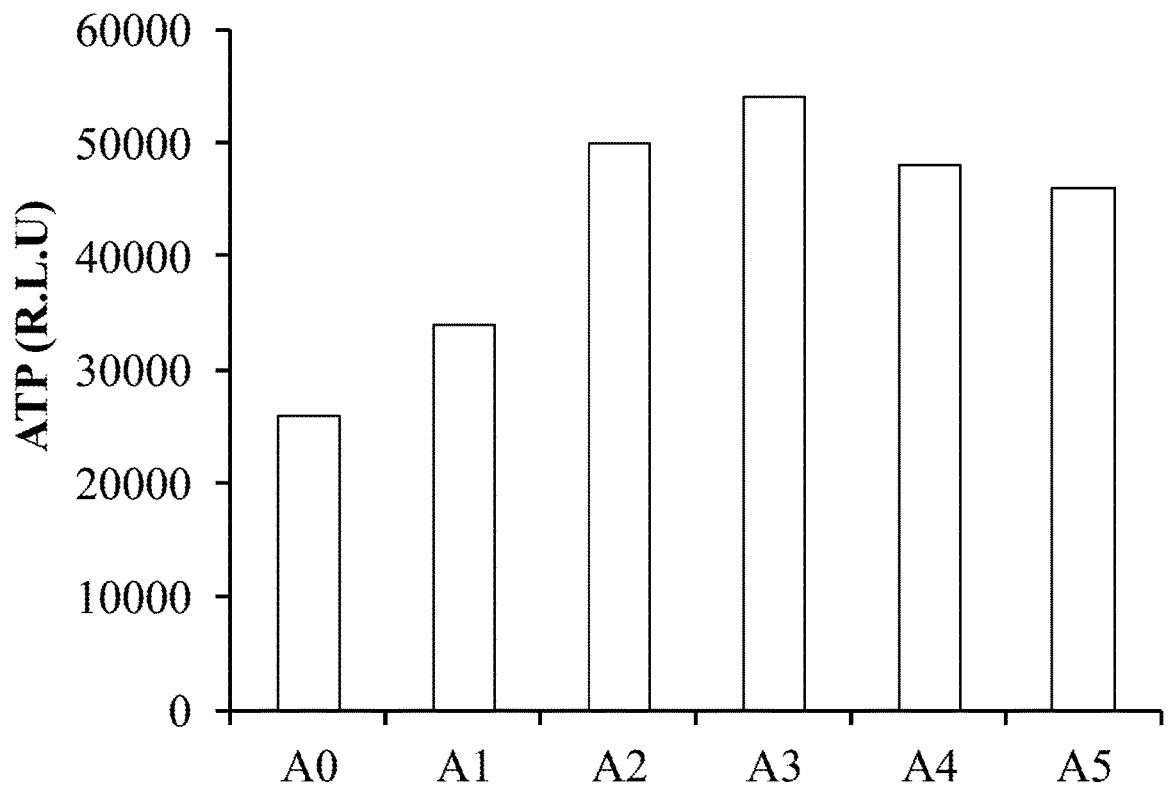
FIG. 2 depicts a bar chart representing ATP level in macrophage J774A.1 cells of groups A0-A5 in trial (A).

Referring to FIG. 2, treatment of propanamide can effectively elevate ATP level in the J774A.1 cells, suggesting propanamide has effect on elevation of cellular ATP. Moreover, when the concentration is below 4 μM, the ATP production shows dose-dependent response to propanamide.

Trial (B).

The increase of cellular ATP can change the activity of macrophage, inhibiting the production of the proinflammatory cytokine, TNF-α, as well as the inflammation. Therefore, the J774A.1 cells of groups B1-B5 were treated by propanamide shown in TABLE 2. After 15 minutes, 200 ng/ml lipopolysaccharide (LPS) was used to induce the inflammation in the J774A.1 cells of groups B1, B3 and B5. The medium of the J774A.1 cells was collected, and the TNF-α level in the medium was detected by a commercial kit.

TABLE 2

| group | LPS | propanamide (μM) |
|---|---|---|
| B0 | − | 0 |
| B1 | + | 0 |
| B2 | − | 4 |
| B3 | + | 4 |
| B4 | − | 40 |
| B5 | + | 40 |

Figure 3:
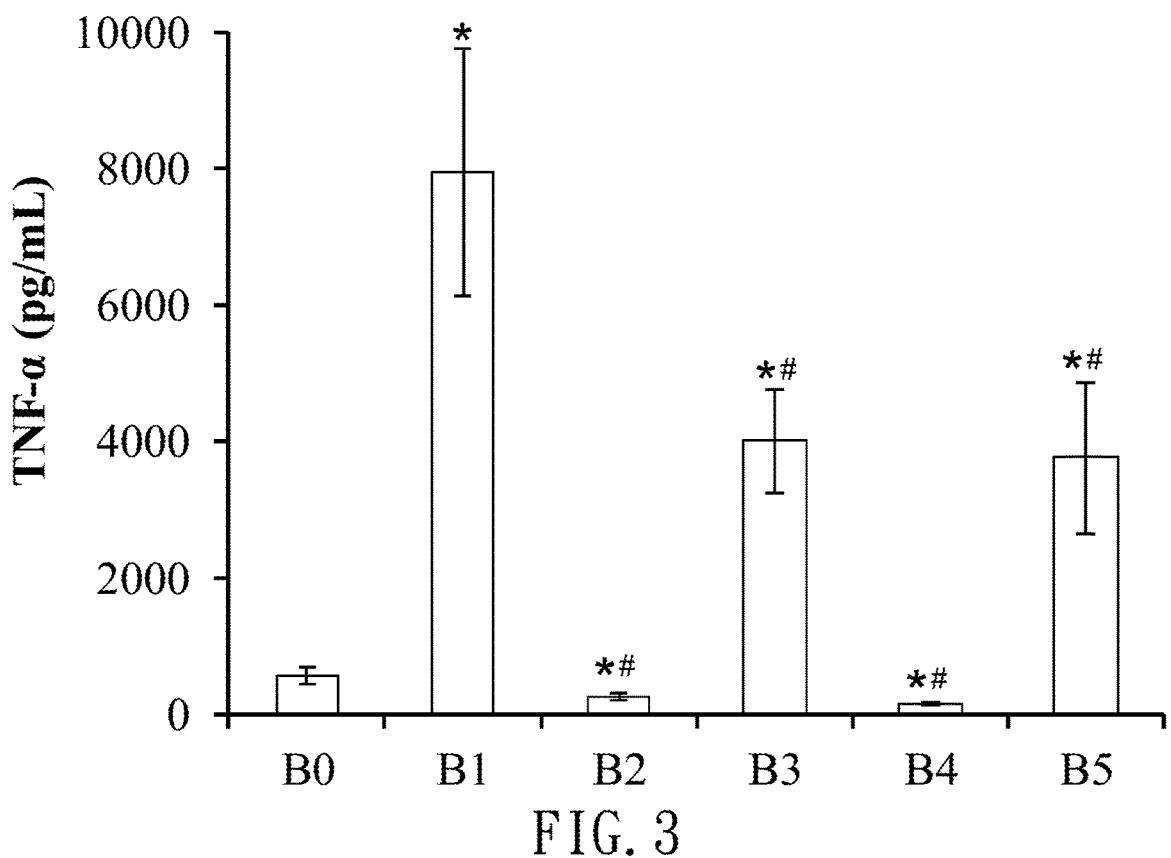
FIG. 3 depicts a bar chart representing tumor necrosis factor-a (TNF-α) level in medium secreted by J774A.1 cells of groups B0-B5 in trial (B). (*$P<0.05$, compared with group B0; #$P<0.05$, compared with group B1).

Referring to FIG. 3, the treatment of propanamide can effectively inhibit the production of TNF-α induced by LPS (groups B3 and B5). Moreover, the treatment of propanamide can also inhibit the production of TNF-α, which is not induced by LPS (groups B2 and B4), suggesting propanamide has effect on anti-inflammation.

Trial (C).

In general, cells store excess energy in form of lipid. About 55% of energy lost in the process of ATP synthesis by the mitochondrion. Therefore, the improvement of the activity of ATP synthesis can decrease the storage of the excess energy in form of lipid, even reducing the accumulation of visceral fat.

Male ICR mice were used as the animal model in Trial (C). As shown in TABLE 3, obese mice of groups C1-C2 were induced by feeding high fat diet for 17 weeks. The obese mice of group C1 were then fed by the high fat diet for another 2 weeks, while the obese mice of group C2 were fed by the high fat diet containing 3 ppm propanamide for further 2 weeks. The normal mice of group C0 were fed by normal diet for 19 weeks. After 19 weeks, the mice of groups C0-C2 were sacrificed, and the effect of propanamide on reducing the accumulation of visceral fat was estimated by weight of epididymal fat (% of body weight).

TABLE 3

| group | diet | propanamide (ppm) |
|---|---|---|
| C0 | normal | 0 |
| C1 | high fat | 0 |
| C2 | high fat | 3 |

Figure 4:
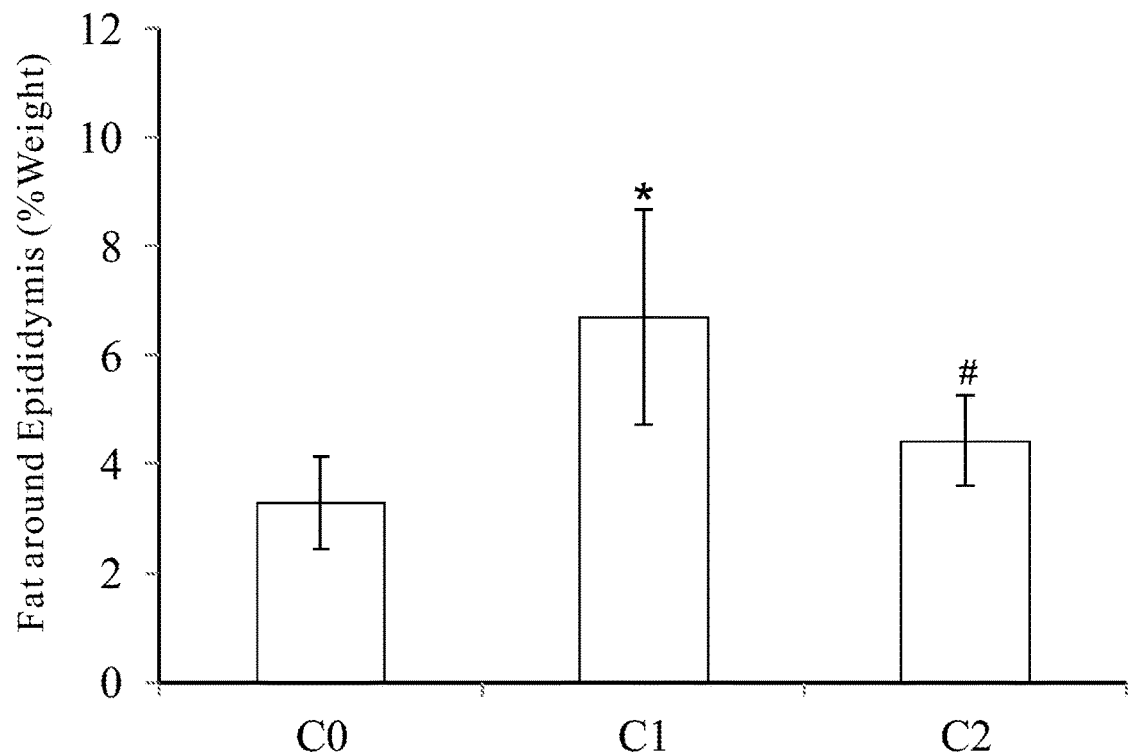
FIG. 4 depicts a bar chart representing the weight percentage of fat around epididymis of mice of groups C0-C2 in trial (C). (*$P<0.05$, compared with group C0; #$P<0.05$, compared with group C1).

Referring to FIG. 4, the weight percentage of epididymal fat of the obese mice fed by the high fat diet (group C1) increased significantly, while the weight percentage of epididymal fat of the obese mice fed by the high fat diet containing propanamide (group C2) was similar to that of the normal mice fed by the normal diet (group C0). That is, the administration of propanamide can effectively reduce the accumulation of visceral fat.

Figure 5:
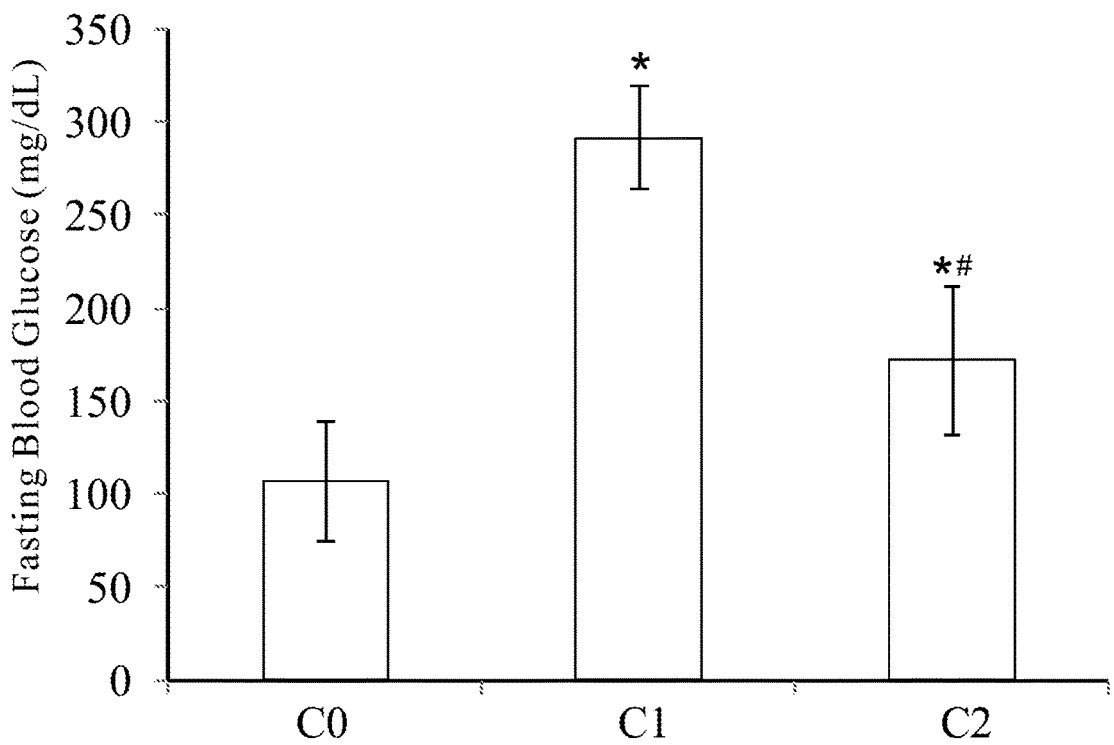
FIG. 5 depicts a bar chart representing level of fasting blood glucose of mice of groups C0-C2 in trial (C). (*$P<0.05$, compared with group C0; #$P<0.05$, compared with group C1).

Before being sacrificed, the mice of groups C0-C2 were fasted for 18 hours, and the levels of fasting blood glucose of the mice were measured. Referring to FIG. 5, the levels of fasting blood glucose of the obese mice fed by the high fat diet (group C1) were higher than that of the normal mice fed by the normal diet (group C0). Moreover, the levels of fasting blood glucose of the obese mice fed by the high fat diet containing propanamide (group C2) decreased significantly, suggesting the administration of propanamide can effectively improve obesity-induced hyperglycemia.

Trial (D).

Wistar male rats were used as the animal model in Trial (D). As shown in TABLE 4, obese rats of groups D1-D3 were induced obesity by feeding high fat diet for 19 weeks. The obese rats of group D1 were then fed by the high fat diet without propanamide for another 4 weeks (total 23 weeks), while the obese rats of group D2 and D3 were fed by the high fat diet respectively containing 1 ppm and 3 ppm propanamide for further 4 weeks, The normal rats of group D0 were fed by normal diet for 23 weeks (total 23 weeks). At the $22^{th}$ week, the oral glucose tolerance tests (OGTT) were performed as following: the rats of groups D0-D3 were fasted for 18 hours, and then were administered a 20% glucose solution (2 g glucose/kg body weight) by gavage. Blood samples were collected and the glucose concentrations were detected at 0, 30, 60, 90, and 120 minutes after glucose loading.

TABLE 4

| Group | Diet | propanamide (ppm) |
|---|---|---|
| D0 | Normal | 0 |
| D1 | high fat | 0 |
| D2 | high fat | 1 |
| D3 | high fat | 3 |

Figure 6A:
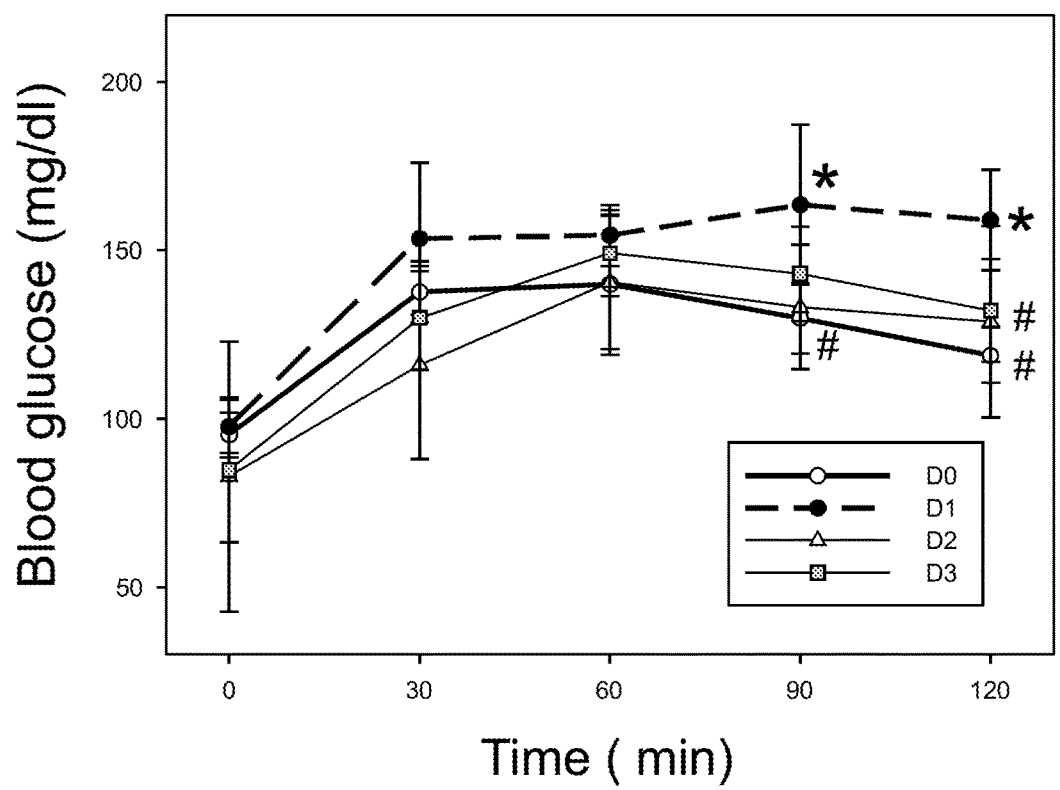
FIG. 6a depicts a curve chart representing the variations of blood glucose during performance of oral glucose tolerance test (OGTT) in rats of groups D0-D3 in trial (D). (*$P<0.05$, compared with group D0 at the same time point; #$P<0.05$, compared with group D1 at the same point).

FIG. 6a shows the curve of blood glucose variation after glucose loading in the obese rats fed by the high fat diet (groups D1, D2, and D3) and the normal rats fed by the normal diet (group D0). At the time point of 90 minutes to 120 minutes, the blood glucose in the obese rats of group D1 was evidently higher than that in the normal rats of group D0 and the obese rats of groups D2. Especially at the time point of 120 minutes, the blood glucose in the obese rats of groups D2 and D3 groups was significantly lower than that in the obese rats of group D1.

Figure 6B:
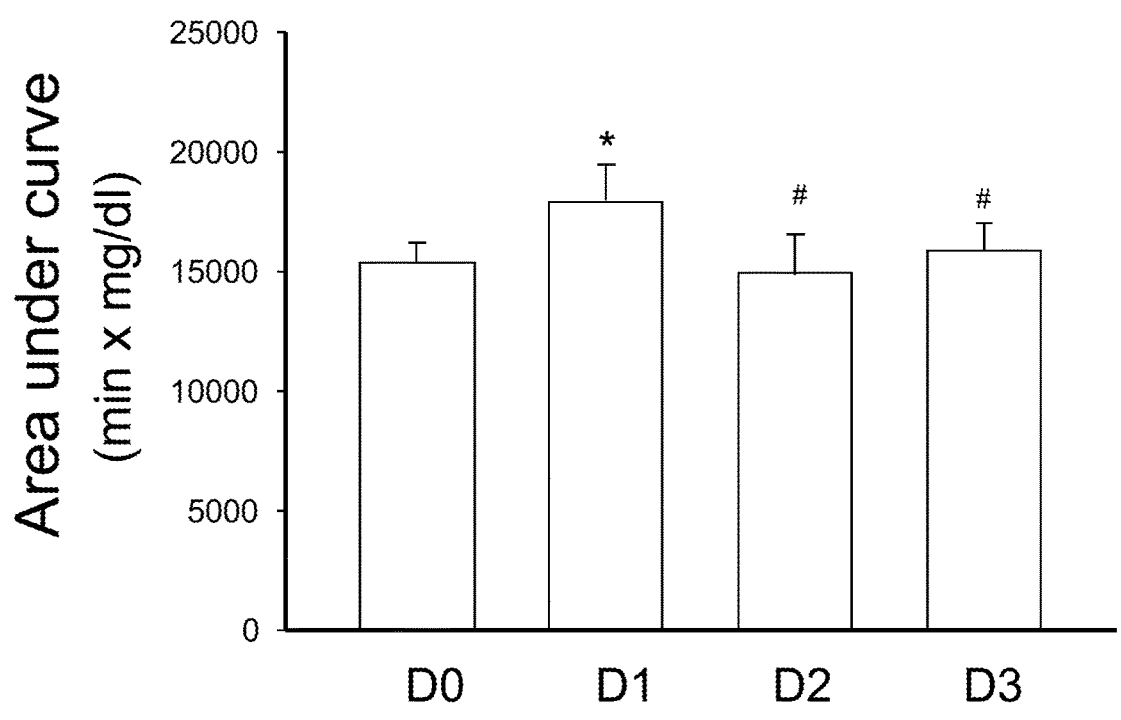
FIG. 6b depicts a bar chart representing the area under curve (AUC) of OGTT from FIG. 6a, which summarized the results of the glucose tolerance in rats of groups D0-D3 in trial (D). (*$P<0.05$, compared with group D0; #$P<0.05$, compared with group D1).

Moreover, as shown in FIG. 6b, the area under curve (AUC) of blood glucose of the obese rats fed by the high fat diet containing 1 and 3 ppm propanamide (groups D2 and D3) decreased significantly, as compared with the normal rats of group D0. These results suggested that the treatment of propanamide can effectively improve obesity-induced glucose intolerance.

Figure 7:
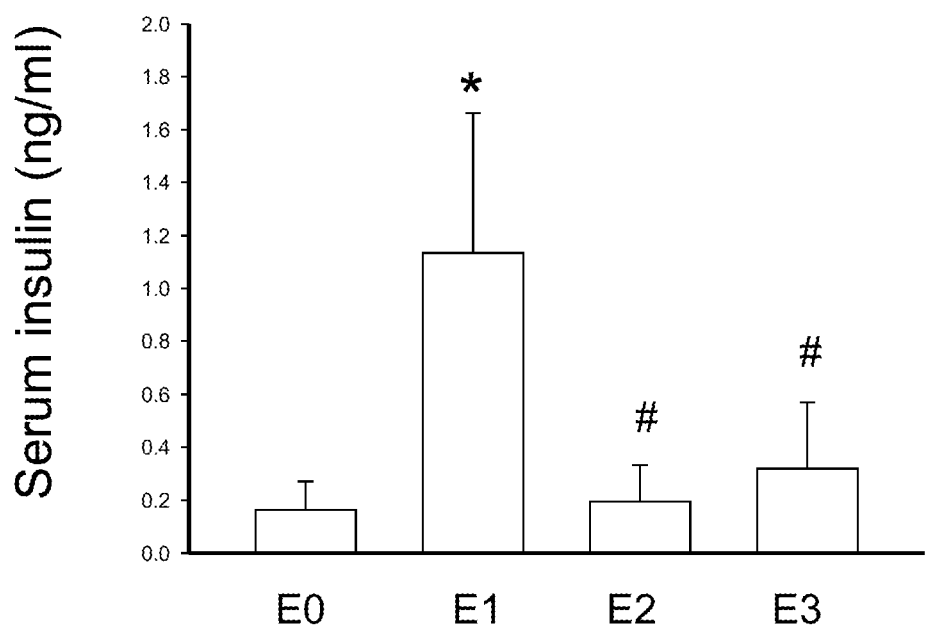
FIG. 7 depicts a bar chart representing the level of fasting serum insulin of rats of groups D0-D3 in trial (D). (*$P<0.05$, compared with group D0; #$P<0.05$, compared with group D1).

At $23^{th}$ week, the rats of groups D0-D3 were fasted for 18 hours before scarification, and the serum were analyzed the level of insulin. As FIG. 7 shown, the fasting serum insulin were evidently elevated in obese rats (group D1), but the serum insulin were reduced to normal level after treatment of 1 and 3 ppm propanamide (groups D2 and D3). These results suggested that the treatment of propanamide can effectively improve obesity-induced hyperinsulinemia.

In addition, according to "Estimating the Maximum Safe Starting Dose in Initial Clinical Trials for Therapeutics in Adult Healthy Volunteers" published by U.S. Food and Drug Administration, and human equivalent dose of a 60 kilogram human is 694-923 µg based on the amount of feed consumed by the mice per day and the body weight of the mice, converted to administering dosage is about 11.56-15.38 µg/kg.

Accordingly, by the use of propanamide, the activity of ATP synthesis can be effectively elevated.

Moreover, by increase of ATP synthesis, not only inflammation can be decreased, but also accumulation of visceral fat, as well as obesity-induced hyperglycemia and hyperinsulinemia, can be prevented. Our results suggested that the treatment of propanamide can effectively attenuate obesity-induced insulin resistance.

Although the invention has been described in detail with reference to its presently preferable embodiment, it will be understood by one of ordinary skill in the art that various modifications can be made without departing from the spirit and the scope of the invention, as set forth in the appended claims.

What is claimed is:

1. A method of improvement of insulin sensitivity in obese patients, comprising:
   administering propanamide to a subject in need thereof to increase activity of ATP synthesis, decreasing inflammation, reducing accumulation of visceral fat and ameliorating obesity-induced hyperglycemia and hyperinsulinemia.

2. The method of improvement of insulin sensitivity in obese patients as claimed in claim 1, wherein propanamide is orally administered to the subject.

3. The method of improvement of insulin sensitivity in obese patients as claimed in claim 1, wherein propanamide is administered to the subject in a dosage of 11.56-15.38 µg/kg/day.

4. The method of improvement of insulin sensitivity in obese patients as claimed in claim 1, wherein propanamide is administered to the subject postprandially.

* * * * *